United States Patent [19]

Bjornestol et al.

[11] Patent Number: 5,363,901
[45] Date of Patent: Nov. 15, 1994

[54] METHOD FOR DETECTING PINHOLES IN CONTINUOUSLY CAST BILLETS

[75] Inventors: Karl O. Bjornestol, Kristiansand; Jan T. Malmo, Trondheim; Yngve Strom, Oslo; Eiolf Vikhagen, Trondheim, all of Norway

[73] Assignee: Elkem Technology a/s

[21] Appl. No.: 979,616

[22] Filed: Nov. 19, 1992

[30] Foreign Application Priority Data

Nov. 22, 1991 [NO] Norway ............... 914574

[51] Int. Cl.$^5$ .................. B22D 11/00; G01N 21/89
[52] U.S. Cl. .................. 164/451; 164/150.1; 356/237
[58] Field of Search ............ 164/451, 150; 356/237

[56] References Cited

U.S. PATENT DOCUMENTS

| 2,758,712 | 8/1956 | Linderman ............ 356/237 X |
| 3,176,306 | 3/1965 | Burns ............ 356/237 X |
| 3,715,476 | 2/1973 | Watanabe et al. . |
| 3,781,117 | 12/1973 | Laycak et al. ............ 356/237 X |
| 3,795,452 | 3/1974 | Bourdelais et al. . |
| 4,028,728 | 6/1977 | Sharp . |
| 4,223,346 | 9/1980 | Neiheisel et al. ............ 356/237 X |

FOREIGN PATENT DOCUMENTS

| 0153565 | 9/1985 | European Pat. Off. . |
| 0335155 | 10/1989 | European Pat. Off. . |
| 0365874 | 5/1990 | European Pat. Off. . |
| 0370527 | 5/1990 | European Pat. Off. . |
| 0452905 | 10/1991 | European Pat. Off. . |
| 2528740 | 12/1983 | France ............ 164/150 |
| 2911578 | 9/1979 | Germany ............ 164/150 |
| 3200007 | 7/1983 | Germany ............ 164/150 |
| 3205698 | 9/1983 | Germany ............ 356/237 |
| 60-146134 | 8/1985 | Japan ............ 356/237 |
| 63-30164 | 2/1988 | Japan ............ 164/451 |
| 2-151351 | 6/1990 | Japan ............ 164/451 |
| 20958264A | 10/1982 | United Kingdom ............ 164/150 |

OTHER PUBLICATIONS

Patent Abstracts of Japan, vol. 10, No. 334 (P-515) (2390) 13 Nov. 1986 & JP-A-61-139743 (Hitachi) 27 Jun. 1986.

Fairchild Camera and Instrument Corp., Model CCD1300 Line-Scan Camera Subsystem Instruction Manual, Section 7, 1977.

*Primary Examiner*—J. Reed Batten, Jr.
*Attorney, Agent, or Firm*—Lucas & Just

[57] ABSTRACT

Continuously cast metal billets are continuously passed by a symmetric light source comprising a plurality of single light sources arranged in a circle or in another way such that the light falls substantially symmetrically on the part of the surface of the metal billet which is to be detected in such a way that the surface of the metal billet which faces the light source is illuminated except for pinholes. Reflected light from the surface of the billet is detected by a linescan camera arranged centrally in relation to the light source, which camera has a scanning direction normal to the direction of movement of the metal billet, whereby pinholes are detected by registration of reflected light intensity below a preset threshold value.

14 Claims, 2 Drawing Sheets

METHOD FOR DETECTING PINHOLES IN CONTINUOUSLY CAST BILLETS

The present invention relates to a method for detection of pinholes in the surface of continuously cast metal billets, especially continuously cast steel and aluminium billets.

Pinholes are open holes in the surface of continuously cast metal billets, which holes are mainly caused by gas formation in the metal during continuous casting. Metal billets having pinholes exceeding a certain size cannot be used. Up till now detection of pinholes has been done manually. This is an uncertain, slow and costly method.

It is an object of the present invention to provide an automatic and continuous method for detecting and marking pinholes in continuously cast metal billets, especially in continuously cast steel billets and aluminium billets.

Accordingly, the present invention relates to a method for detection of pinholes in continuously cast metal billets which method is characterized in that continuously cast metal billets are continuously passed by a symmetric light source comprising a plurality of single light sources arranged in a circle or in another way such that the light falls substantially symmetrically on the part of the surface of the metal billet which is to be detected in such a way that the surface of the metal billet which faces the light source is illuminated except for pinholes, reflected light from the surface of the billet is detected by means of a linescan camera arranged centrally in relation to the light source, which camera has a scanning direction normal to the direction of movement of the metal billet, whereby pinholes are detected by registration of reflected light intensity below a preset threshold value.

According to a preferred embodiment of the present invention the symmetric light source has a circular geometry with a circle diameter exceeding the width of the metal billet.

In order to ensure detection of all pinholes having diameters above a preset value, the transport speed of the metal billet is adjusted in such a way in relation to the scanning speed of the camera that the metal billet is transported a distance that is less than the minimum pinhole diameter to be detected from the start of one scan to the start of the next scan. Alternatively the scanning speed of the camera is adjusted in such a way in relation to the transportation speed of the metal billet that the metal billet, from the start of one scan to the start of the next scan, is transported a length which is less than the preset minimum pinhole diameter to be detected.

According to a preferred embodiment of the present invention the transport speed of the metal billet and/or the scanning speed of the camera is adjusted in such a way that the metal billet is transported less than half of the preset minimum pinhole diameter from the start of one scan to the start of the next scan. The light intensity registered by the linescan camera is preferably forwarded to a computer wherein the position and the size of detected pinholes are calculated and stored and/or shown directly on a video screen.

By the present invention it has been found that pinholes in continuously cast metal billets can be detected automatically and very fast and the positions and sizes of the pinholes in a metal billet can be stored in a computer, whereby the pinholes can be removed by metal working later.

By the method of the present invention, pinholes having a diameter down to 0.5 mm can be detected in a safe way.

The present invention will now be further described with reference to the accompanying drawings, wherein, FIG. 1 schematically shows an apparatus which can be used by the method of the present invention.

Figure 1:
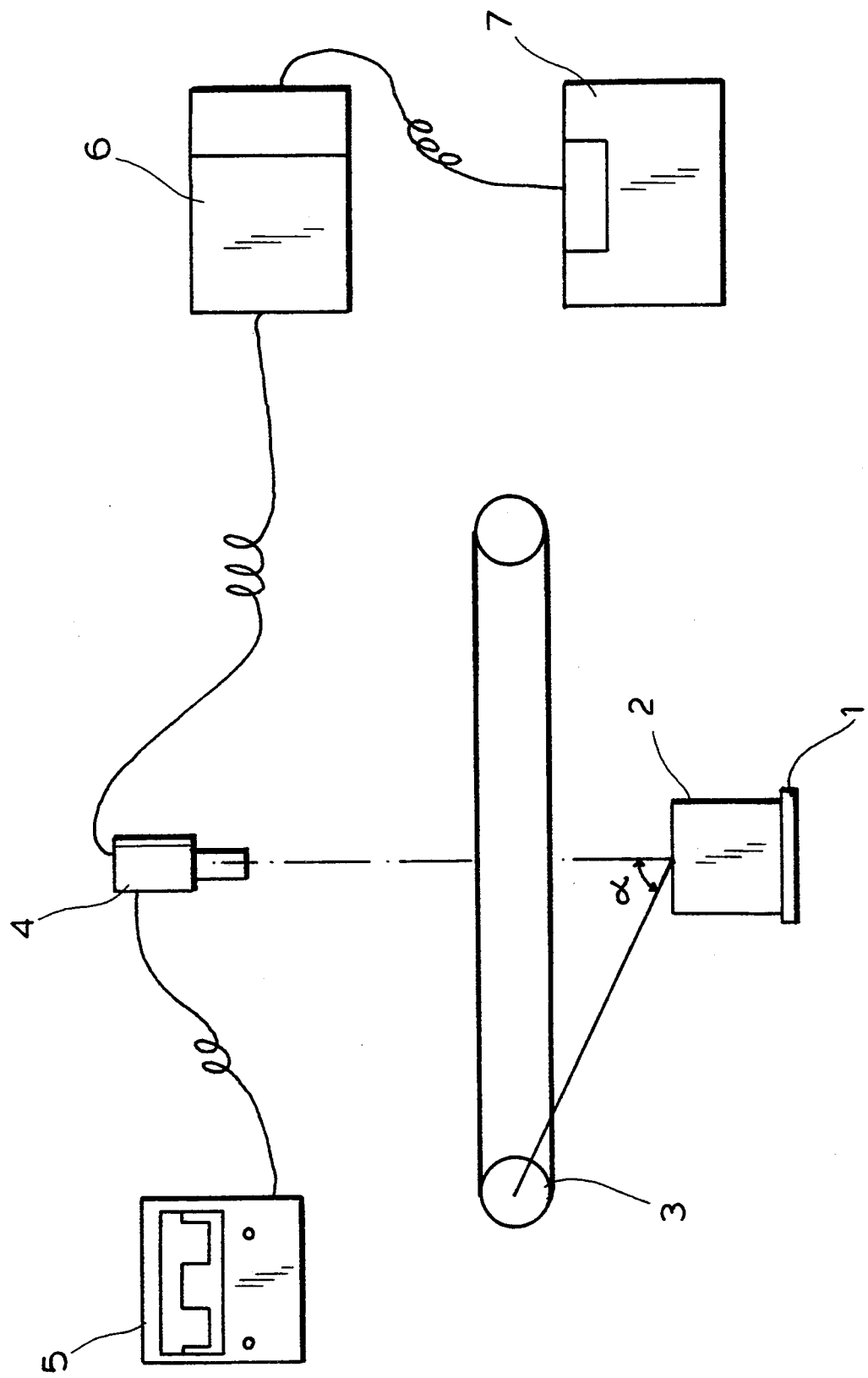

The apparatus shown in FIG. 1 comprises a transport rail 1 for transport of a continuously cast metal billet 2. Above the metal billet 2 there is arranged a light source 3, which gives a symmetric illumination geometry. Above and centrally located in relation to the light source 3 there is arranged a linescan camera 4 for detecting reflected light from the surface of the metal billet 2. The camera 4 is used to scan reflected light in a direction normal to the moving direction of the metal billet 2.

An oscilloscope 5 is connected to the camera 4 and is used to adjust the focus of the camera 4. The threshold value is adjusted in such a way that the intensity of reflected light from parts of the surface of the metal billet having no pinholes is above the threshold value. When the camera registers a reflected light intensity below the threshold value, this is registered as a pinhole. The positions of the registered pinholes are registered by a computer 6 and the data can be stored and/or can be shown directly on a video screen 7.

EXAMPLE

Figure 2:
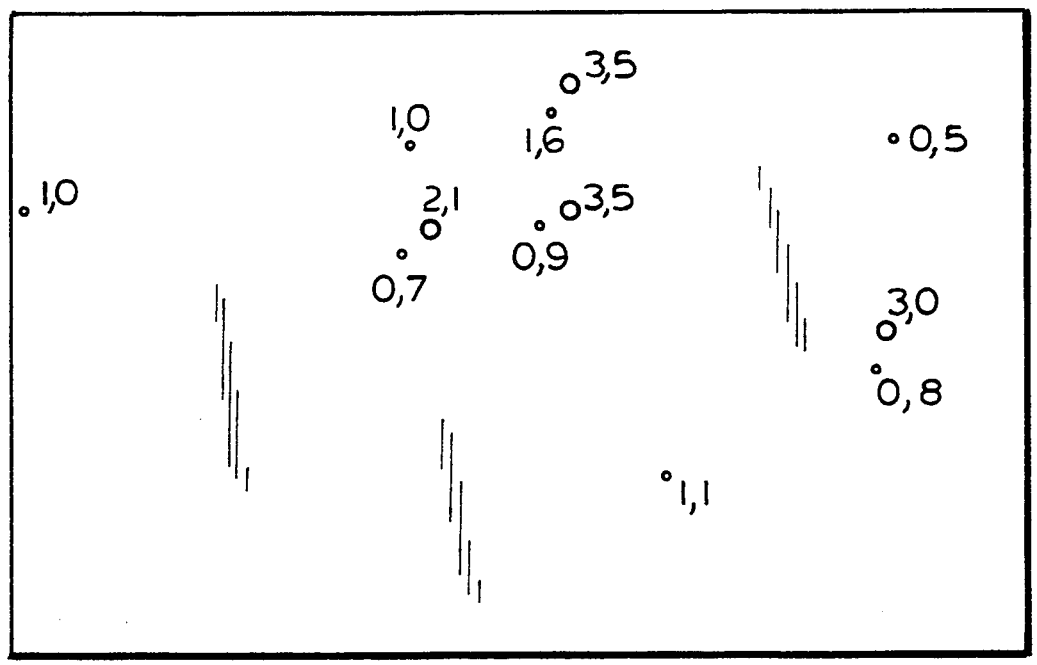
FIG. 2 shows the surface of a steel billet with marked pinholes.

A piece of continuously cast steel billet having a length of 25 cm and a width of 8.8 cm was tested in accordance with the method of the present invention. By visual inspection 12 pinholes were found situated on one of the surfaces of the test piece. The test piece is schematically shown in FIG. 2 with pinholes and the diameter of each pinhole given in mm. The test piece was tested in an apparatus corresponding to the apparatus shown in FIG. 1.

The light source was a circular, symmetric light source having a diameter of 40 cm and the illumination angle against the test piece was 63°.

A linescan camera having a linescan frequency of 1500 Hz was arranged 112 cm above the surface of the test piece and the registrations of reflected light were forwarded from the camera to a computer where the data was treated. The result was shown directly on a video screen.

Figure 3:
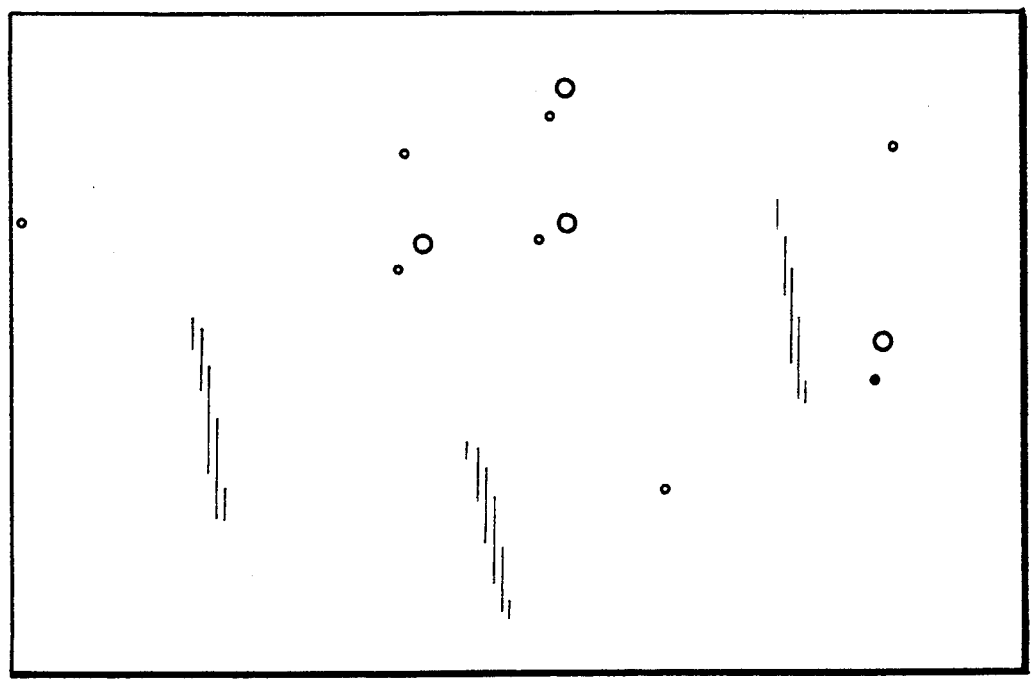
FIG. 3 shows the result of pinhole detection of the billet of FIG. 2.

The transport speed for the metal billet was 320 ram/second and the steel specimen was transported 0.28 mm between the start of one linescan to the start of the next linescan. The result is shown on FIG. 3. As can be seen from FIG. 3, all 12 pinholes were clearly detected.

We claim:

1. A method for detecting a pinhole in a continuous cast metal billet comprising the steps of:
   (a) moving a continuous cast metal billet in a direction under a light source and a linescan camera, said light source being symmetrically arranged above said billet so as to cause light to illuminate a surface area of said billet in a substantially symmetrical manner;

(b) illuminating a surface area of said billet with said light source as said billet moves under said light source such that light reflected from that portion of said surface area of said billet that has a pinhole has an intensity lower than the intensity of light reflected from that portion of said surface area of said billet that has no pinhole;

(c) scanning said surface area of said billet illuminated by said light source with said linescan camera in a direction which is normal to the direction of movement of said billet, said linescan camera being centrally positioned in relation to said light source, and said camera scanning at a speed such that said billet moves a distance under said linescan camera less than a preset minimum pinhole diameter from the start of one scan to the start of the next scan;

(d) adjusting said camera by means of an oscilloscope connected to said camera such that the intensity of the light reflected from that portion of said surface area of said billet that has a pinhole is below a preset threshold level and the intensity of the light reflected from that portion of said surface area of said billet that has no pinhole is above said preset threshold level; and (e) detecting said pinhole in said billet by means of a computer by determining those portions of said billet where the light reflected from said surface area of said billet is below said threshold level.

2. The method of claim 1 wherein the distance moved by said billet is less than half of the preset minimum pinhole diameter from the start of one scan to the start of the next scan.

3. The method of claim 1 wherein said preset minimum pinhole diameter is about 0.5 mm.

4. The method of claim 1 wherein the distance moved by said billet is less than half of about 0.5 mm.

5. The method of claim 1 wherein said light source is circular in geometry and has a circle diameter exceeding the width of said billet.

6. The method of claim 5 wherein the linescan camera is located inside the circular light source.

7. A method for detecting a pinhole in a continuous cast metal billet comprising the steps of:

(a) moving a continuous cast metal billet in a direction under a light source and a linescan camera, said light source being arranged above said billet so as to cause light to illuminate a surface area of said billet in a substantially symmetrical manner;

(b) illuminating a surface area of said billet with said light source as said billet moves under said light source such that light reflected from that portion of said surface area of said billet that has a pinhole has an intensity lower than the intensity of light reflected from that portion of said surface area of said billet that has no pinhole;

(c) scanning said surface area of said billet illuminated by said light source with said linescan camera in a direction which is normal to the direction of movement of said billet, said linescan camera being centrally positioned in relation to said light source, and said camera scanning at a speed such that said billet moves a distance under said linescan camera less than a preset minimum pinhole diameter from the start of one scan to the start of the next scan;

(d) adjusting said camera such that the intensity of the light reflected from that portion of said surface area of said billet that has a pinhole is below a preset threshold level and the intensity of the light reflected from that portion of said surface area of said billet that has no pinhole is above said preset threshold level; and (e) detecting said pinhole in said billet by means of a computer by determining those portions of said billet where the light reflected from said surface area of said billet is below said threshold level.

8. The method of claim 7 wherein said light source is arranged in a symmetrical manner above said billet.

9. The method of claim 7 wherein said camera is adjusted by means of an oscilloscope connected to said camera.

10. The method of claim 7 wherein the distance moved by said billet is less than half of the preset minimum pinhole diameter from the start of one scan to the start of the next scan.

11. The method of claim 7 wherein said preset minimum pinhole diameter is about 0.5 mm.

12. The method of claim 7 wherein the distance moved by said billet is less than half of about 0.5 mm.

13. The method of claim 8 wherein said light source is circular in geometry and has a circle diameter exceeding the width of said billet.

14. The method of claim 13 wherein the linescan camera is located inside the circular light source.

* * * * *